(12) United States Patent
Berggren et al.

(10) Patent No.: US 11,324,275 B2
(45) Date of Patent: May 10, 2022

(54) WELDING HELMET

(71) Applicant: 3M INNOVATIVE PROPERTIES COMPANY, St. Paul, MN (US)

(72) Inventors: Martin Berggren, Tällberg (SE); Thomas B. Stenvall, Sundborn (SE)

(73) Assignee: 3M Innovative Properties Company, St. Paul, MN (US)

( * ) Notice: Subject to any disclaimer, the term of this patent is extended or adjusted under 35 U.S.C. 154(b) by 117 days.

(21) Appl. No.: 16/645,715

(22) PCT Filed: Sep. 19, 2018

(86) PCT No.: PCT/IB2018/057228
§ 371 (c)(1),
(2) Date: Mar. 9, 2020

(87) PCT Pub. No.: WO2019/058285
PCT Pub. Date: Mar. 28, 2019

(65) Prior Publication Data
US 2020/0297060 A1    Sep. 24, 2020

(30) Foreign Application Priority Data
Sep. 22, 2017 (EP) .................. 17192507

(51) Int. Cl.
*A61F 9/06* (2006.01)
*A42B 3/20* (2006.01)
*A42B 3/22* (2006.01)

(52) U.S. Cl.
CPC ............ *A42B 3/20* (2013.01); *A42B 3/225* (2013.01); *A61F 9/06* (2013.01)

(58) Field of Classification Search
CPC ........... A42B 3/20; A42B 3/225; A42B 3/105; A61F 9/06
See application file for complete search history.

(56) References Cited

U.S. PATENT DOCUMENTS

| 7,093,302 | B1 * | 8/2006 | Burns .................. A61F 9/06 2/8.1 |
| 10,226,383 | B2 * | 3/2019 | Ambring ........... A41D 13/0518 |
| 2012/0216340 | A1 * | 8/2012 | Asta .................. A42B 3/105 2/422 |
| 2014/0298557 | A1 | 10/2014 | Townsend, Jr. |
| 2016/0074230 | A1 | 3/2016 | Sernfaelt |

FOREIGN PATENT DOCUMENTS

| CN | 106859847 | | 6/2017 | |
| EP | 3466287 A1 * | | 4/2019 | ............ A42B 3/225 |
| EP | 3 528 656 | | 8/2019 | |
| GB | 2034171 | | 6/1980 | |
| WO | WO-2018002435 A1 * | | 1/2018 | ............ A61F 9/06 |

OTHER PUBLICATIONS

Extended EP Search Report for EP Application No. 17192507.6, dated Mar. 16, 2018, 2 pages.
International Search Report for PCT International Application No. PCT/IB2018/057228, dated Dec. 10, 2018, 6 pages.

* cited by examiner

*Primary Examiner* — Tajash D Patel
(74) *Attorney, Agent, or Firm* — Gregg H. Rosenblatt

(57) ABSTRACT

A welding helmet (1) with a head suspension system, a protective shield (2) and a movable visor (3). The protective shield forms a see-through window. The welding helmet further has a first neck shield (6). The protective shield forms a lower end at which the first neck shield is removably attachable.

14 Claims, 4 Drawing Sheets

WELDING HELMET

FIELD OF THE INVENTION

The invention relates to a welding helmet and in particular to a welding helmet that has a first and/or second neck shield that are removably attachable to a protective shield of the welding helmet and are therefore exchangeable. The invention further relates to a kit of parts comprising the welding helmet and a plurality of neck shields.

BACKGROUND ART

Welding Helmets are typically used in the mechanical and industrial art to protect welders from harmful irradiation emitted from the welding arc and from splashes, sparks and particles that may be ejected from a welding area. Welding helmets typically can be suspended on the head of a wearer, so that the wearer has both hands available for welding and handling of workpieces.

Some welding helmets are furnished with an automatic darkening filter. An automatic darkening filter commonly has a switchable filter that automatically changes from a light-state to a dark-state in response to incident light generated by the welding arc. Thus, upon ignition of the welding arc the switchable filter automatically changes to the dark-state and protects the welder's eyes and face from the irradiation emitted from welding arc. Once the welding is interrupted or ended the switchable filter automatically changes to the light-state so that the user can see through the filter at normal light conditions.

Accordingly there are welding helmets that stay in position on a wearer's head independent from the actual welding actions, for example during locating of the electrode toward the workpiece to be welded or during handling. To provide a wearer of such a welding helmet with sufficient freedom to move the head, the portion of the welding helmet that covers the wearer's face typically should not extend too far in an area of the wearer's neck. A shield that covers the whole neck typically impacts the wearing comfort, in particular when the wearer attempts to move the head downward (with the chin toward the chest). On the other hand it is desirable to protect the wearer's neck.

There are welding helmets that have a flexible neck shield. For example US 2016/0074230 A1 discloses an eye-protection headgear including a rigid visor with a window bearing an optical filter, and with a flexible fabric bib and a flexible fabric cap.

Although there is already a variety of welding helmets there is still a need for a welding helmet that provides for a maximized wearing comfort and that still fulfills the safety requirements in the field of welding.

SUMMARY OF THE INVENTION

In one aspect the invention relates to a welding helmet that comprises a head suspension system and a protective shield. The protective shield has or forms a see-through window. The welding helmet further comprises a first neck shield. The protective shield forms a lower end and the first neck shield is removably attachable to the lower end of the protective shield.

The invention is advantageous in that it provides a welding helmet which can be customized according to a wearer's needs. In particular the invention provides for a welding helmet that can be equipped with differently shaped neck shields. The invention provides for example for a welding helmet that can be used in a forced air mode with a neck shield that entirely covers the front of a wearer's neck, and that can be used in a non-air mode in which air is permitted to reach the wearer's mouth and/or nose via a gap or space left between the wearer's chin and chest by a different neck shield.

In one embodiment the welding helmet has a movable visor. The movable visor is preferably movably, for example pivotably, suspended relative to the see-through window. Therefore the movable visor can be preferably positioned between a first position in which the movable visor covers the see-through window and a second position in which the movable visor uncovers the see-through window.

The see-through window is preferably positioned and sized so that a wearer of the welding helmet can see through the see-through window with both eyes when the wearer wears the welding helmet. The movable visor may be pivotably suspended at the protective shield, at the head suspension system or via a connector that connects the head suspension system, the protective shield and the movable visor.

The protective shield has a lower end. The term "lower end" refers to the end of the protective shield that is arranged next to a wearer's chin when the welding helmet is worn. The protective shield (in the context of being worn) extends upwards from that lower end to an area at least above the wearer's eyes, preferably to an area at the top of the wearer's head.

In one embodiment the removable attachment is based on a snap connection. The protective shield preferably has one or more retention structures and the first neck shield preferably has corresponding counter structures for mating with the retention structures of the protective shield. The one or more retention structures may particularly be provided at the lower end of the protective shield. Thereby the first neck shield may be removably attachable to the lower end of the protective shield. The retention structures may be receptacles, for example recesses or holes, and the counter structures may be flaps (or vice versa). In one embodiment the retention structures and the counter structures in combination provide for a snap connection. Each flap may for example have an L-shaped structure. This means that that flap may protrude in one direction and may have a further protrusion extending laterally of that direction.

In one embodiment the welding helmet has a second neck shield. Hence in this embodiment the welding helmet has a first and a second neck shield. The first neck shield preferably has a predetermined permanent shape. Further the second neck shield preferably exhibits flexible properties providing the second neck shield with a self-adapting shape. In particular the second neck shield may have a bib that exhibits flexible properties providing the bib with a self-adapting shape. The term "self-adapting" thereby means that the neck shield or bib deforms by its own weight toward the shape of a surface on which the neck shield or the bib is placed.

In an embodiment the first neck shield is sized to extend at a first length toward a user's chest, when the welding helmet is worn. Further the second neck shield is sized to extend at a greater second length toward a user's chest, when the welding helmet is worn. Further the welding helmet may have a third neck shield. In this embodiment the second neck shield may have the same length or generally the same length as the first neck shield, but the third neck shield may have a greater length than the second neck shield.

In one embodiment the second neck shield has an attachment frame and a bib. The attachment frame is removably attachable to the protective shield. Preferably, the counter retention structures of the attachment frame correspond in structure to the counter retention structures of the first neck shield. Therefore the first and second neck shield (and optionally further neck shields) preferably have identical interface for removably attaching to the lower end of the protective shield. Preferably the attachment frame has a greater bending stiffness than the bib. Further, the attachment frame may be made of the same material as the first neck shield. The first neck shield may exhibit a bending stiffness that is 50 times higher than that of the bib. The bib may be formed by at least one of a fabric, leather, a non-woven or an elastomer.

In one embodiment the see-through window in the protective shield is closed by a fixed visor. The fixed visor is preferably fixedly positioned relative to the see-through window. In particular the fixed visor may be attached at the protective shield via a visor frame that holds the fixed visor in place. That visor frame may be attached to the protective shield.

In one embodiment the movable visor comprises an automatic darkening filter. In an embodiment in which the movable visor is not present or optional, the fixed visor may comprise an automatic darkening filter. The automatic darkening filter is preferably based on two liquid crystal cells. The liquid crystal cells are electrically switchable between a light-state and a dark-state. The two liquid crystal cells are preferably arranged optically in sequence. Each liquid crystal cell comprises two transparent substrates with a liquid crystal layer arranged between. Each substrate is provided with an alignment layer that is in contact with the liquid crystal layer. The alignment layers provide for a default uniform alignment of the liquid crystals. Further, the two liquid crystal cells preferably comprise three polarizers, one of which being arranged between the two liquid crystal cells and the other two being arranged on outer sides. The outer side polarizers may be arranged with their light polarizing orientation in the same or substantially the same direction, whereas the inner polarizer may be oriented with its light polarizing orientation 90 degrees or substantially 90 degrees relative to the outer polarizers.

In the light-state the transmittance of the automatic darkening filter may be within a range of about 1% to about 20%, in more particular within a range of about 5% to about 10%, whereas in the dark-state the transmittance of the automatic darkening filter may be within a range of about 0.0005% to about 0.1%.

In one embodiment the movable or fixed visor comprises a permanent optical filter (instead of an automatic darkening filter). Such an optical filter may have a permanent transmittance within a range of about 0.0005% to about 0.1%. Thus the permanent optical filter provides a permanent dark-state.

In a further embodiment the welding helmet has a sensor for detecting light, as for example light emitted from the welding arc. The sensor and the automatic darkening filter are functionally interconnected so that light above a predetermined light intensity detected by the sensor causes the automatic darkening filter to switch to the dark-state and the absence or non-detection of light above the predetermined light intensity causes the automatic darkening filter to switch to the light-state.

In one embodiment the protective shield is pivotable relative to the head suspension system. The head suspension system and the protective shield may for example be connected via a hinge that provides a pivot. Therefore a wearer can lift or pivot the protective shield up, for example for handling workpieces or the like.

In one embodiment the welding helmet further comprises an air connector for supplying air between the protective shield and a wearer's head. Accordingly the welding helmet can be used in a forced air mode when an air supply is connected to the air connector. Further the same welding helmet can be used in a non-air mode when the air connector is not connected to an air supply. The first neck shield may be used in the non-air mode. In this case the first neck shield is preferably sized to leave a space between a wearer's chin and chest to permit air to reach the wearer's mouth and nose from that space. The second neck shield may be used in the forced air mode. In this case the second neck shield is preferably sized to cover the area between the wearer's chin and chest to protect the wearer's neck from potentially harmful radiation emitted by the welding arc. The air may in this case be provided to the wearer's mouth and nose via the air supply. Accordingly the welding helmet of the invention is flexible in use and can be customized with respect to the mode of use, in particular with respect to the forced air mode and the non-air mode.

In a further aspect the invention relates to a kit of parts, comprising a welding helmet according to the invention and a first neck shield and a second neck shield. The welding helmet and the first and second neck shield may correspond to any of the embodiments as disclosed herein.

In particular the welding helmet of the kit of parts comprises a head suspension system and a protective shield. The protective shield forms a see-through window. The kit further comprises a first neck shield and a second neck shield. The protective shield forms a lower end at which either one of the first and second neck shield is selectively attachable in a removable manner.

The welding helmet which the kit of parts refers to is preferably further configured as described herein.

In a further embodiment the kit of parts may comprise a plurality of different neck shields. The neck shields may particularly differ in their length. The length refers to a dimension at which the neck shield extends in a direction from a wearer's chin toward the wearer's chest.

In a further aspect the invention relates to a method of configuring a welding helmet. The method comprises the steps of:
 providing a welding helmet that comprises a head suspension system and a protective shield forming a see-through window;
 providing a first neck shield and a different second neck shield, each being configured for a removable attachment to a lower end of the protective shield;
 selecting one of the first and second neck shield; and
 attaching the selected first or second neck shield at the lower end of the protective shield.

The welding helmet which the method refers to is preferably further configured as described herein.

In one embodiment the first neck shield has a predetermined permanent shape and the second neck shield has a bib exhibiting flexible properties providing the bib with a self-adapting shape. This means that the first neck shield is more rigid than the second neck shield or than the bib of the second neck shield. The first neck shield is preferably sized to extend at a first length toward a user's chest, when the welding helmet is worn. Further, the second neck shield is sized to extend at a greater second length toward a user's chest, when the welding helmet is worn.

DETAILED DESCRIPTION OF THE INVENTION

Figure 1:
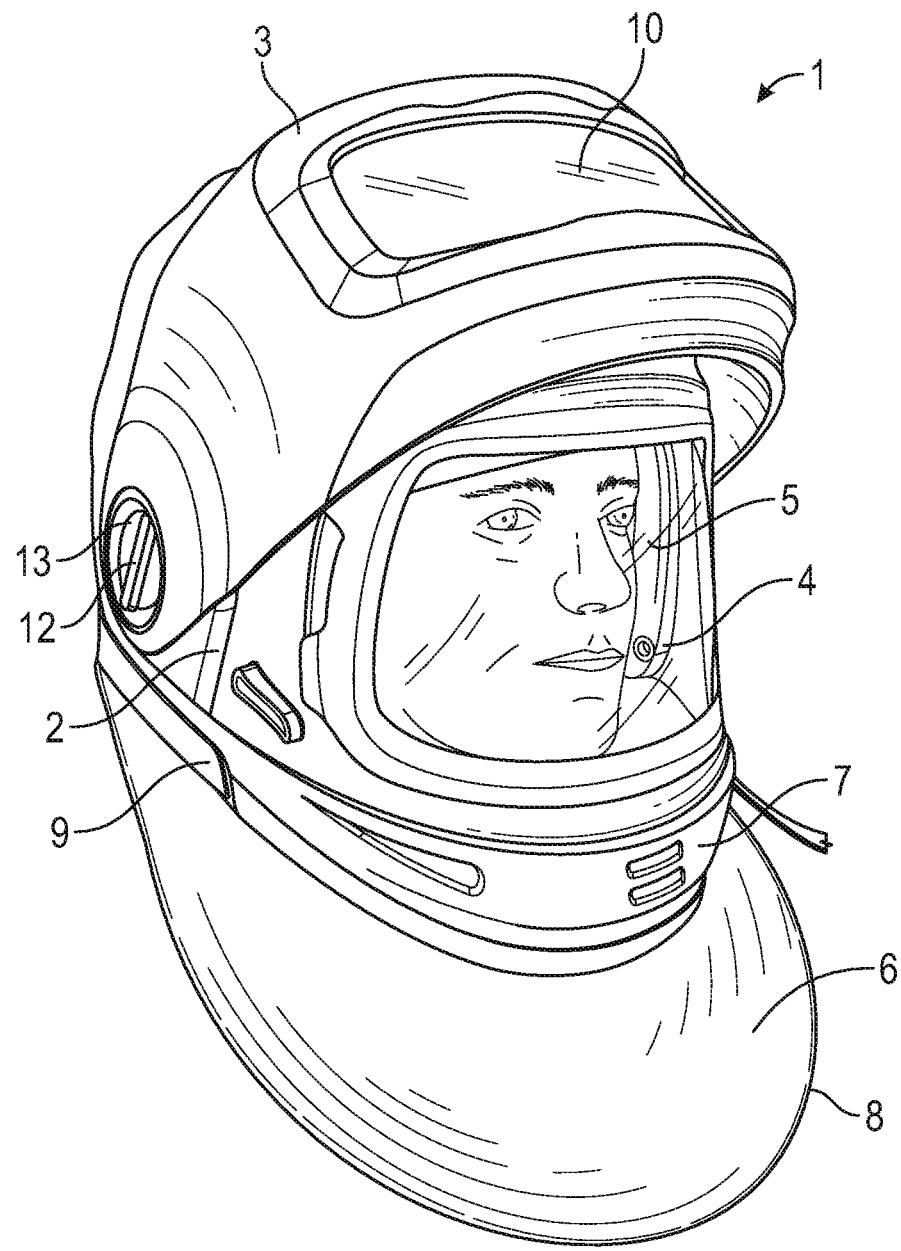
FIG. 1 is a perspective view of a welding helmet according to an embodiment of the invention.

FIG. 1 shows a welding helmet 1 which has a protective shield 2 and a movable visor 3. The protective shield 2 is sized and shaped to cover a wearer's face and the upper part and lateral sides of the wearer's head. The movable visor 3 is arranged on an outside of the protective shield 2. Further the movable visor 3 is pivotably suspended at the welding helmet 1 relative to the see-through window. The movable visor 3 is thus pivotable so that it can be positioned between a first position (not shown in this Figure) in which the movable visor covers the see-through window and a second position (as shown in this Figure) in which the movable visor 3 uncovers the see-through window. The movable visor 3 is suspended at a pivot mechanism 13 which has a knob 12 for adjusting a friction between the movable visor 3 and the protective shield 2. Accordingly the knob 12 allows for retaining the movable visor 3 and the protective shield 2 relative to each other so that the movable visor 3 is prevented from moving by its own weight (for example from the first toward the second position).

The movable visor 3 comprises an automatic darkening filter 10. The automatic darkening filter 10 allows a welder to safely observe the welding arc during welding. In the example the automatic darkening filter 10 is based on two liquid crystal cells. The liquid crystal cells are electrically switchable between a light-state and a dark-state. When switched in the dark-state, the automatic darkening filter 10 blocks a significant amount of light from being transmitted therethrough. This enables a user to observe a welding arc by seeing through the automatic darkening filter 10 without risking to be exposed to harmful light radiation from the welding arc. In the light-state the automatic darkening filter 10 permits a significant amount of light to be transmitted therethrough. Thus, the automatic darkening filter 10 in the light-state allows the user to see under ambient light conditions (in the absence of the welding arc). The two (or more) liquid crystal cells are arranged optically in sequence. This provides for multiplying the darkening effect (in particular in the dark-state) and thus a sufficient eye protection from light radiation.

Further, the welding helmet 1 comprises at least one light sensor (not shown) and electronic circuitry that causes the liquid crystal cells to switch dependent on light recognized by the light sensor(s). In particular, the light sensor may provide a signal to the electronic circuitry depending on the light sensed by the light sensor. The signal provided by the light sensor can typically be correlated to the intensity of light sensed by the light sensor. The electronic circuitry is set up to control the switching of the automatic darkening filter to the dark-state in case the light intensity (and optionally an additional frequency or pulsation) detected by the light sensor is within a predetermined range of values or exceeds a predetermined value. Further, the electronic circuitry is set up to control the switching of the automatic darkening filter to the light-state in case the light intensity detected by the light sensor is outside the predetermined range of values or falls below a predetermined value.

The protective shield 2 of the welding helmet 1 forms a see-through window 4 that is closed by a fixed visor 5. The fixed visor 5 is formed by a clear polymeric panel, which in the example is made of polycarbonate. The fixed visor 5 is fixed at the protective shield 2 and covers, in particular seals, the see-through window 4. The fixed visor 5 may for example be used to protect a wearer of the welding helmet 1 during grinding works. Further, in the first position of the movable visor 3 the see-through window 4 (with the fixed visor 5) overlaps with the movable visor 3 so that a wearer of the welding helmet 1 can see through both, the see-through window 4 (with the fixed visor 5) and the movable visor 3.

The welding helmet further has a neck shield 6. The neck shield 6 provides for protecting a wearer's neck from harmful light as for example emitted from a welding arc, and from particles, for example splashes or particles as they may be ejected during welding and/or grinding. The neck shield 6 is attached at a lower end 7 of the protective shield 2. The attachment of the neck shield is reversible. This means that the neck shield 6 is removable from the protective shield 2. In particular the neck shield 6 is removable from the protective shield 2 without damaging or breaking any of the neck shield 6 or the protective shield 2. In the example the neck shield 6 has a bib 8 which is flexible. The bib 8 in the example is made of a fabric, in particular a fabric. The neck shield 6 further has an attachment frame 9 at which the bib 8 is fixed. The neck shield 6 of the example corresponds to the "second neck shield" as referred to in the Summary of the invention.

Figure 2:
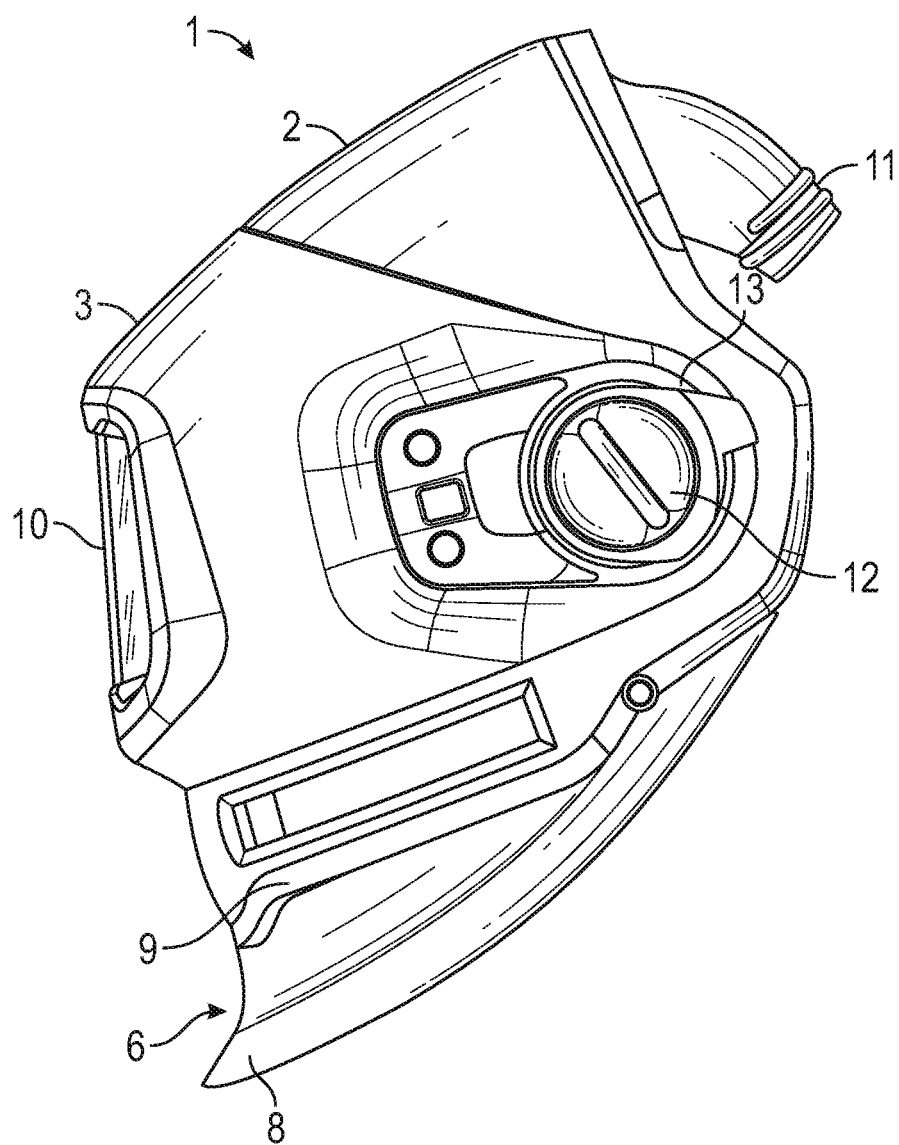
FIG. 2 is a side view of a welding helmet having a second neck shield according to an embodiment of the invention.

FIG. 2 shows the same welding helmet 1 as shown in FIG. 1 in a side view. The welding helmet 1 has an inlet 11 for connecting the welding helmet 1 with an air supply via a hose (not shown). Such an air supply may for example by a powered air purifying unit as known in the field of powered air purifying respirators (PAPRs). Thus, a wearer of the welding helmet 1 can be supplied with fresh air forced between the protective shield 2 and the wearer's head (and face).

Figure 3:
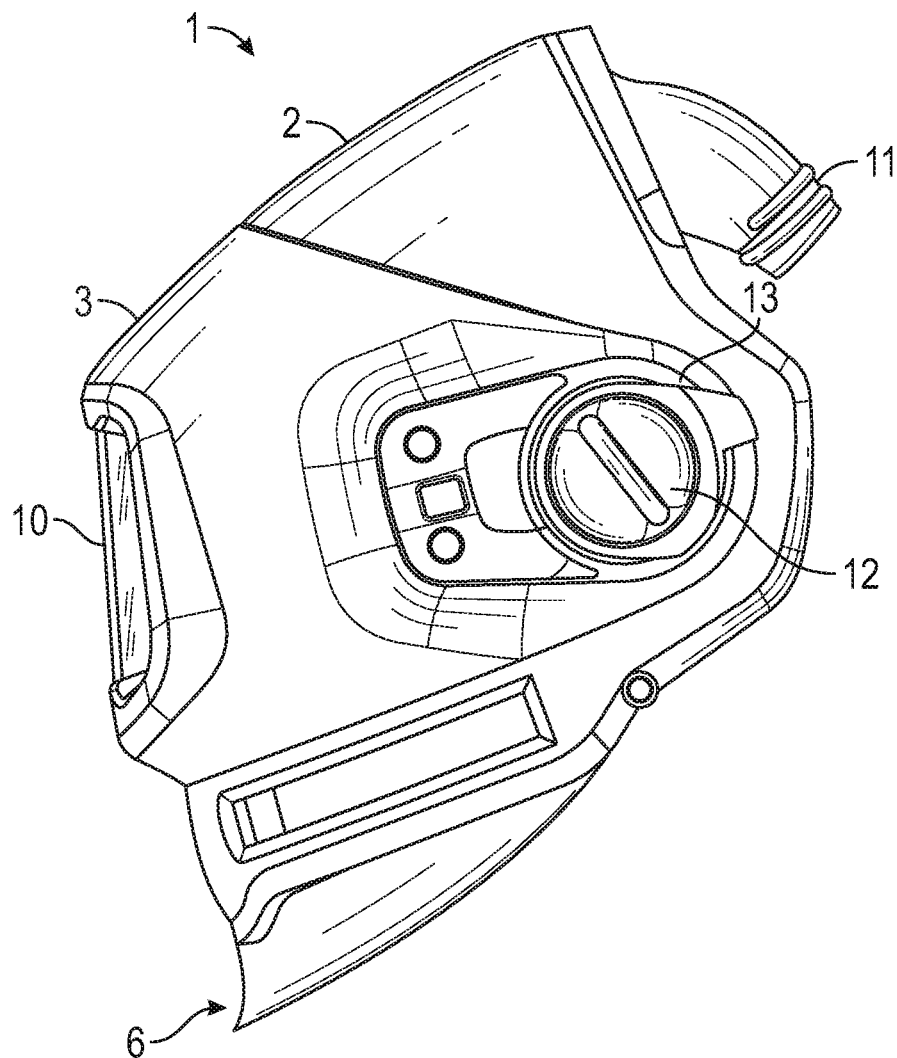
FIG. 3 is a side view of a further welding helmet a first neck shield according to an embodiment of the invention.

FIG. 3 shows the same welding helmet 1 as shown in FIGS. 1 and 2 but with a different neck shield 6. The neck shield 6 in the example shown in FIG. 3 has a predetermined permanent shape. This means that the neck shield 6 of this example is more rigid than the bib of the neck shield of the neck shield shown in FIGS. 1 and 2. The neck shield 6 of this example corresponds to the "first neck shield" as referred to in the Summary of the invention.

Figure 4:
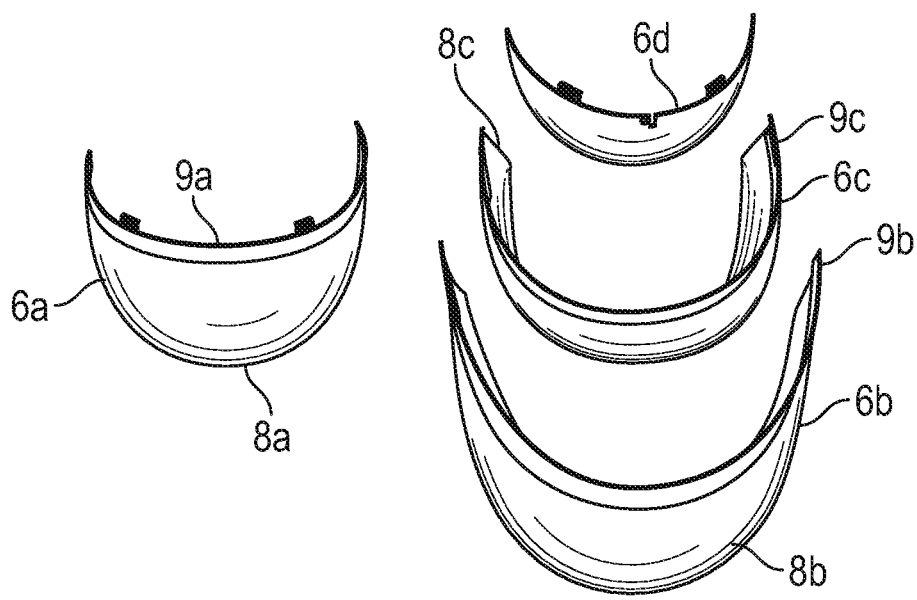
FIG. 4 is a perspective view of a plurality of different neck shields according to an embodiment of the invention.
Figure 5:
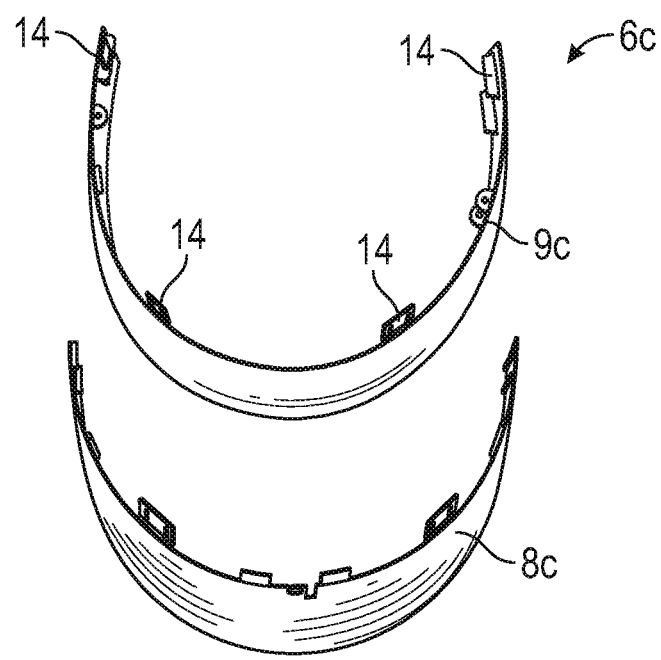
FIG. 5 is an exploded view of a neck shield according to an embodiment of the invention.

FIG. 4 shows a plurality of different neck shields 6a, 6b, 6c and 6d as they may be used with the present invention. The plurality of different neck shields 6a-6d in combination form a kit of parts from which a wearer of the welding helmet (shown in FIGS. 1-3) can select any of the neck shields 6a-6d for use with the welding helmet. The neck shields 6a to 6c each comprises an attachment frame 9a-9c and a bib 8a-8c, respectively. By way of example the structure of the neck shield 6c with the attachment frame 9c and the bib 8c is illustrated in FIG. 5. As illustrated, the kit of parts comprises neck shields 6a-6c with the individual neck shields 6a-6c having bibs 8a-8d of different lengths. For example, the bib 8b of the neck shield 6b is longer than the bib 8a of the neck shield 6a, and the bib 8c of the neck shield 6c is longer than the bib 8b of the neck shield 6b. The length of the bib 8a-8c thereby refers to a dimension at which the respective bib 8a-8c extends from the respective attachment frame 9a-9c, respectively. Such length further refers to a dimension at which the respective bib 8a-8c extends in a direction from a wearer's chin toward the wearer's chest. Therefore the wearer can customize the welding helmet by using one of the plurality of neck shields 6a-6d with the welding helmet.

The neck shield 6d is made of only one material, whereas the neck shields 6a-6c are each made of two different materials. Further, neck shield 6d is more rigid than the bib 8a-8c of the respective neck shield 6a-6c. The rigidity can be physically expressed by the bending stiffness. In that regard the neck shield 6d (which corresponds to the first neck shield as referred to herein) exhibits a bending stiffness that is at least 50 times of the bending stiffness of the bib 8a-8c of the neck shields 6a-6c, respectively. The neck shields 6a-6c thereby each correspond to the second neck shield as referred to herein.

In FIG. 5 the neck shield 6c is shown in further detail in an exploded view. In particular the attachment frame 9c has a plurality of flaps 14 which are configured to form a snap connection with corresponding receptacles (not shown) in the protective shield. Accordingly, the receptacles in the protective shield form retention structures and the flaps 14 form corresponding counter structures. The skilled person will recognize that some or all of the receptacles may be arranged at the neck shields and the corresponding flaps may be arranged at the protective shield. It has however been found that the arrangement of the receptacles at the protective shield provides a more robust design, because the likelihood of the flaps to break is higher when arranged at the protective shield than when arranged at the neck shield.

The invention claimed is:

1. A welding helmet comprising:
a head suspension system; and
a protective shield forming a see-through window, the protective shield having a lower end disposed adjacent to a user's chin region when the helmet is worn, the lower end including one or more retention structures configured to removably receive corresponding counter structures formed on both a first neck shield and a second neck shield, wherein the first neck shield has a predetermined permanent shape and the second neck shield has a bib exhibiting flexible properties providing the bib with a self-adapting shape, wherein the second neck shield includes an attachment frame and the bib, wherein the attachment frame is configured to engage with the one or more retention structures and is removably attachable to the protective shield, and wherein the attachment frame has a greater bending stiffness than the bib,
wherein either the first or second neck shield can be attached to the lower end.

2. The welding helmet of claim 1, comprising a movable visor being movably suspended relative to the see-through window for positioning between a first position in which the movable visor covers the see-through window and a second position in which the movable visor uncovers the see-through window.

3. The welding helmet of claim 2, wherein the movable visor comprises an automatic darkening filter.

4. The welding helmet of claim 1, wherein the first neck shield is sized to extend at a first length toward a user's chest, when the welding helmet is worn, and the second neck shield is sized to extend at a second length, greater than the first length, toward a user's chest, when the welding helmet is worn.

5. The welding helmet of claim 4, wherein the bib is formed by at least one of a fabric, leather, a non-woven or an elastomer.

6. The welding helmet of claim 1, wherein the removable attachment is based on a snap connection.

7. The welding helmet of claim 1, wherein the see-through window in the protective shield is closed by a fixed visor that is fixedly positioned relative to the see-through window.

8. The welding helmet of claim 1, wherein the protective shield is pivotable relative to the head suspension system.

9. The welding helmet of claim 1, further comprising an air connector for supplying air between the protective shield and a wearer's head.

10. A kit of parts, comprising a welding helmet that comprises a head suspension system and a protective shield forming a see-through window, the kit further comprises a first neck shield and a second neck shield, and wherein the protective shield forms a lower end at which either one of the first and second neck shield is selectively attachable in a removable manner, wherein the second neck shield includes an attachment frame and the bib, wherein the attachment frame is configured to engage with the one or more retention structures and is removably attachable to the protective shield, and wherein the attachment frame has a greater bending stiffness than the bib.

11. A method of configuring a welding helmet, comprising the steps of:
providing a welding helmet that comprises a head suspension system and a protective shield forming a see-through window;
providing a first neck shield and a different second neck shield, each being configured for a removable attachment to a lower end of the protective shield, wherein the second neck shield includes an attachment frame and the bib, wherein the attachment frame is configured to engage with the one or more retention structures and is removably attachable to the protective shield, and wherein the attachment frame has a greater bending stiffness than the bib;
selecting one of the first and second neck shield; and
attaching the selected first or second neck shield at the lower end of the protective shield.

12. The method of claim 10, wherein the first neck shield has a predetermined permanent shape and the second neck shield has a bib exhibiting flexible properties providing the bib with a self-adapting shape.

13. The method of claim 10, wherein the first neck shield is sized to extend at a first length toward a user's chest, when the welding helmet is worn, and the second neck shield is sized to extend at a second length, greater than the first length, toward a user's chest, when the welding helmet is worn.

14. The welding helmet of claim 1, wherein a bending stiffness of the first neck shield is at least 50 times a bending stiffness of the bib.

* * * * *

UNITED STATES PATENT AND TRADEMARK OFFICE
CERTIFICATE OF CORRECTION

PATENT NO. : 11,324,275 B2
APPLICATION NO. : 16/645715
DATED : May 10, 2022
INVENTOR(S) : Martin Berggren It is certified that error appears in the above-identified patent and that said Letters Patent is hereby corrected as shown below:

In the Claims

Column 8,
Line 27, delete "the bib" and insert -- a bib -- therefor.
Line 41, delete "the bib" and insert -- a bib -- therefor.

Signed and Sealed this
Twentieth Day of June, 2023

Katherine Kelly Vidal
*Director of the United States Patent and Trademark Office*